US009770220B2

(12) United States Patent
Stearns et al.

(10) Patent No.: US 9,770,220 B2
(45) Date of Patent: Sep. 26, 2017

(54) INTEGRATED MICROTOMOGRAPHY AND OPTICAL IMAGING SYSTEMS

(71) Applicant: Caliper Life Sciences, Inc., Waltham, MA (US)

(72) Inventors: Daniel G. Stearns, Los Altos, CA (US); David G. Nilson, Walnut Creek, CA (US); Bradley W. Rice, Danville, CA (US)

(73) Assignee: Caliper Life Sciences, Inc., Waltham, MA (US)

( * ) Notice: Subject to any disclaimer, the term of this patent is extended or adjusted under 35 U.S.C. 154(b) by 0 days.

(21) Appl. No.: 15/098,819

(22) Filed: Apr. 14, 2016

(65) Prior Publication Data

US 2016/0228079 A1    Aug. 11, 2016

Related U.S. Application Data

(63) Continuation of application No. 13/164,640, filed on Jun. 20, 2011, now Pat. No. 9,314,218.

(51) Int. Cl.
*A61B 6/00* (2006.01)
*G01N 23/04* (2006.01)
(Continued)

(52) U.S. Cl.
CPC .......... *A61B 6/4417* (2013.01); *A61B 5/0035* (2013.01); *A61B 5/0073* (2013.01);
(Continued)

(58) Field of Classification Search
CPC ............ G01N 2223/419; G01N 23/046; A61B 6/4429; A61B 6/547; A61B 6/588
See application file for complete search history.

(56) References Cited

U.S. PATENT DOCUMENTS 6,870,897 B2    3/2005    Sari-Sarraf et al.
7,016,465 B2 *  3/2006    Kamegawa ........... G01N 23/046
                                                           378/19
(Continued)

FOREIGN PATENT DOCUMENTS

JP    2002-181737    6/2002    ............ G01N 23/04
JP    2005-351879    12/2005   ............ G01N 23/04
(Continued)

OTHER PUBLICATIONS

Da Silva et al., "Coupling X-Ray and optical tomography systems for in vivo examination of small animals", Proceedings of the 29$^{th}$ Annual International Conference of the IEEE EMBS, p. 3335-3338, Aug. 23-28, 2007.
(Continued)

*Primary Examiner* — David J Makiya
*Assistant Examiner* — Dani Fox
(74) *Attorney, Agent, or Firm* — Fish & Richardson P.C.

(57) ABSTRACT

An integrated microtomography and optical imaging system includes a rotating table that supports an imaging object, an optical stage, and separate optical and microtomography imaging systems. The table rotates the imaging object about a vertical axis running therethrough to a plurality of different rotational positions during a combined microtomography and optical imaging process. The optical stage can be a trans-illumination, epi-illumination or bioluminescent stage. The optical imaging system includes a camera positioned vertically above the imaging object. The microtomography system includes an x-ray source positioned horizontally with respect to the imaging object. Optical and x-ray images are both obtained while the imaging object remains in place on the rotating table. The stage and table are included within an imaging chamber, and all components are included within a portable cabinet. Multiple imaging objects can be imaged
(Continued)

simultaneously, and side mirrors can provide side views of the object to the overhead camera.

20 Claims, 8 Drawing Sheets

(51) Int. Cl.
  *A61B 6/03* (2006.01)
  *A61B 6/04* (2006.01)
  *A61B 5/00* (2006.01)
  *G01N 21/76* (2006.01)
(52) U.S. Cl.
  CPC .............. *A61B 6/032* (2013.01); *A61B 6/035* (2013.01); *A61B 6/0457* (2013.01); *A61B 6/508* (2013.01); *A61B 6/5247* (2013.01); *G01N 21/763* (2013.01); *G01N 23/046* (2013.01); *A61B 6/4405* (2013.01); *A61B 2503/40* (2013.01); *G01N 2223/419* (2013.01)

(56) References Cited

U.S. PATENT DOCUMENTS

| 2005/0215873 | A1 | 9/2005 | Peter |
| 2005/0254619 | A1 | 11/2005 | Kamegawa |
| 2006/0118742 | A1 | 6/2006 | Levenson et al. |
| 2006/0268153 | A1 | 11/2006 | Rice et al. |
| 2007/0238957 | A1* | 10/2007 | Yared ............... A61B 5/0059 600/407 |
| 2009/0018451 | A1 | 1/2009 | Bai et al. |
| 2009/0074136 | A1 | 3/2009 | Kamegawa |
| 2009/0324048 | A1 | 12/2009 | Leevy et al. |
| 2011/0112395 | A1 | 5/2011 | Ichikawa et al. |
| 2011/0282181 | A1 | 11/2011 | Wang et al. |
| 2012/0302880 | A1 | 11/2012 | Tian et al. |

FOREIGN PATENT DOCUMENTS

| JP | 2010-236913 | 10/2010 | ............. G01N 21/64 |
| WO | WO 2004/081865 | 9/2004 | |
| WO | WO 2008/024986 | 2/2008 | ............... A61B 6/03 |
| WO | WO 2009/120281 | 10/2009 | ............... A61B 6/00 |
| WO | WO 2012/071682 | 6/2012 | ............. G01N 23/04 |

OTHER PUBLICATIONS

Da Silva et al., "Whole body in vivo examination of small animals by simultaneous X-Rays/optical tomography: comparison between the reconstructions obtained with different types of fluorescent labels", LETI-CEA MINATEC, microTechnologies for Biology and Healthcare Division, SPIE vol. 6629, 662911 (2007).
Zhang et al., "Mico-CT in a Dual-Modality Flourescence/Computed Tomography System for Small Animal Imaging", IEEE Nuclear Science Symposium Conference Record, p. 3735-3737 (2007).
Zhang et al., "Coregistered tomographic x-ray and optical breast imaging: initial results", Journal of Biomedical Optics, vol. 10(2), Mar./Apr. 2005.
Communication from the European Patent Office for European Application No. 12 802.919.6 dated Jul. 2, 2015. (4 pages).
European Search Report for European Patent Application Serial No. 12 80 2919 dated Jun. 3, 2015 (3 pages).
Japanese Office Action for Japanese Application Serial No. 2014-517040 dated Apr. 15, 2016.
European Search Report for European Application No. EP 16 18 8689 dated Jan. 30, 2017 (6 pages).
Canadian Office Action for Canadian Application Serial No. 2,839,872 dated Apr. 18, 2017.

* cited by examiner

INTEGRATED MICROTOMOGRAPHY AND OPTICAL IMAGING SYSTEMS

CROSS-REFERENCE TO RELATED APPLICATIONS

Under 35 U.S.C. §120, this application is a continuation of, and claims the benefit of, U.S. application Ser. No. 13/164,640, filed on Jun. 20, 2011, which is incorporated herein by reference in its entirety.

TECHNICAL FIELD

The present invention relates generally to systems and methods for obtaining multiple types of images of an object, and more particularly to obtaining such images without transferring the object between different imaging systems.

BACKGROUND

There are currently numerous non-invasive imaging techniques that can be used to produce images of a given object. Such techniques include X-rays, magnetic resonance imaging ("MRI"), computed tomography ("CT" or "microtomography") scans, ultrasound and optical imaging using structured light, among others. In addition, various non-invasive optical imaging techniques such as bioluminescence and fluorescence can be used to produce optical images of animal objects, such as in the areas of medical research, pathology, drug discovery and development, and the like. Each such imaging technique has advantages and disadvantages that are useful for different imaging applications. Some techniques are well suited to provide spatial or anatomical information for internal parts, while others are more suited to provide functional information for an activity of interest within an object being imaged. Due to the differing advantages of different types of imaging systems, it has become increasingly desirable to combine the outputs and strengths of multiple imaging systems for a single imaging object.

As one particular example of a multi-modal imaging system, there can be a considerable synergistic advantage to combining x-ray microtomography (also known as computed tomography or CT) imaging and optical tomography to increase the information content of the optical measurements of a given imaging object. In particular, the morphological information obtained by microtomography provides anatomical information that assists the interpretation of the optical data and improves the model for light transport that is required to reconstruct the light source distribution.

Performing optical diffuse tomography reconstruction generally requires a measurement of the surface topography of a three-dimensional imaging object. Previous systems to accomplish such reconstructions have utilized an optical structured light technique to scan the surface of the imaging object and produce a surface mesh. This method often works well, but is limited by complexities like rough fur or dark colors on a given imaging object. Furthermore, the structured light typically only gives the surface topography on the top half of the imaging object. Thus, there can be several inherent drawbacks to some multi-modal imaging systems, at least with respect to those that use structured light as one of the imaging modes.

Furthermore, a single imaging object is often transferred between different imaging systems in many traditional multi-modal imaging systems, such as a combination of x-ray and optical systems. As might be expected, however, the transfer of an imaging object can result in various problems with coordinating the different object images. Imaging object transfer issues can include, for example, jostling or bumping by the person or apparatus moving the object between disparate imaging systems. Further problems can arise where the imaging object is a living animal or specimen, such as a mouse, that would ordinarily be inclined to move on its own during the transfer. Substantial changes in imaging object positioning, muscle flexing and the like during a transfer between imaging systems can then result in images from the second and/or subsequent imaging systems that do not overlap well with images from the first and/or prior imaging systems. Efforts to combine such disparate systems into a single imaging system are quite difficult, due to the different requirements, mechanisms and other items that tend to interfere with each other.

While many systems and methods for providing multiple types of images of a object have generally worked well in the past, there is always a desire to provide new and improved ways to obtain such internal images. In particular, what is desired are systems and methods that can produce multiple types of images of an imaging object without any need to transfer the object between separate imaging systems.

SUMMARY

It is an advantage of the present invention to provide systems and methods that produce multiple types of images of an imaging object without any need to transfer the object between separate imaging systems. Such transfer-less, multi-modal imaging systems can be provided by way of a single imaging system that is adapted to provide two different kinds of imaging on the same imaging object at the same location. In particular, such a single imaging system can include facilities for x-ray imaging and optical tomography in a single location for a single imaging object, which can be rotated to a plurality of different positions at that single location. Specific applications can involve the x-ray imaging being done with respect to one axis, and the optical tomography being done with respect to a different axis that is orthogonal to the x-ray axis. Such configurations allow the multiple imaging modalities to co-exist without interfering with one another, while at the same time enabling a low-cost, compact and portable instrument.

In various general embodiments, a multi-modal imaging system can include a stage adapted to support a separate imaging object at a single location during a multi-modal imaging process, an optical imaging system configured to obtain optical imaging data on the imaging object while the imaging object is on the stage, and a secondary imaging system separate from said optical imaging system and configured to obtain secondary imaging data while the imaging object is on the stage. The optical imaging data and the secondary imaging data can both be obtained while the imaging object remains at the single location. Also, the optical imaging data can be obtained with respect to a first axis running through the imaging object, and the secondary imaging data can be obtained with respect to a second axis running through the imaging object, where the second axis is orthogonal with respect to the first axis.

In various detailed embodiments, the secondary imaging system can be an x-ray imaging system, such as a microtomography imaging system. Further, the first axis can be vertical with respect to the imaging object while the second axis is horizontal with respect to the imaging object. The stage can include transillumination components adapted to transilluminate the imaging object from below. The stage can also or alternatively include a rotating table adapted to support and to rotate the imaging object to a plurality of different rotational positions during the multi-modal imaging process. The secondary imaging system can then be configured to obtain secondary imaging data for the imaging object at each of the plurality of different rotational positions. The rotating table can be adapted to support a plurality of separate imaging objects thereupon, and the optical and secondary imaging systems can be adapted to image the plurality of separate imaging objects simultaneously.

In still further detailed embodiments, the system can include a processing device in logical communication with the both the optical imaging system and the secondary imaging system, with the processing device being adapted to combine imaging data obtained by the optical imaging system with imaging data obtained by the secondary imaging system. An imaging chamber can also be included, and all items can be contained within an outer cabinet that is adapted to contain the stage, the optical imaging system and the secondary imaging system therewithin. Such a cabinet can be readily portable from one location to another. Further detailed embodiments can include one or more mirrors positioned at one or more sides of the imaging object and arranged at an angle with respect to the stage, table or object, such that one or more side views of the imaging object are reflected upward toward the camera.

In various further embodiments, an integrated microtomography and optical imaging system can include an imaging chamber adapted to contain a separate imaging object therewithin, a rotating table located within the imaging chamber and adapted to support the imaging object thereupon, and a separate microtomography imaging system. The rotating table can be adapted to rotate the imaging object about a vertical axis running therethrough to a plurality of different rotational positions during a combined microtomography and optical imaging process. The optical imaging system can include a camera positioned substantially vertically above the imaging object and adapted to obtain optical images of the imaging object with respect to the vertical axis while the imaging object is on the rotating table. The microtomography imaging system can be include an x-ray source and one or more x-ray sensors adapted to receive x-rays from the x-ray source, with the x-ray source being positioned in a substantially horizontal direction with respect to the imaging object on the rotating table. Both the optical images and the x-ray images can be obtained while the imaging object remains within the imaging chamber.

In various detailed embodiments, the multi-modal imaging system can include a trans-illumination system adapted to facilitate transillumination of the imaging object from below, can include an epi-illumination system adapted to facilitate epi-illumination of the imaging object from above, and/or can be adapted to facilitate the bioluminescent imaging of the imaging object. In addition, one or more beam shaping devices can be situated proximate the x-ray source and adapted to shape an x-ray beam emitted therefrom.

The system can also include a processing device in logical communication with both the optical imaging system and the microtomography imaging system, with the processing device being adapted to combine imaging data obtained by the optical imaging system with imaging data obtained by the microtomography imaging system. Such combination of imaging data from the optical and microtomography imaging systems can result in a three-dimensional representation of the separate imaging object. Still further, the entire integrated microtomography and optical imaging system can be readily portable from one location to another, such as where the entire system is contained within a cabinet having wheels thereon.

In further detailed embodiments, the processing device can be further adapted to process x-ray imaging data obtained from the microtomography imaging system to yield a volumetric three-dimensional rendering of the imaging object, segment the x-ray imaging data to determine an x-ray surface mesh of the imaging object, map optical image data obtained from the optical imaging system onto the x-ray surface mesh of the imaging object, and process the surface-mapped optical image data through a diffuse tomography algorithm to determine a three-dimensional distribution of light-emitting sources within the imaging object. The processing device can also be further adapted to determine an anatomical map of tissues within the imaging object using the volumetric microtomography data, and create a heterogeneous tissue property map for use within the optical diffuse tomography algorithm using the anatomical map.

Also, the rotating table can be adapted to support a plurality of mice or other separate imaging objects thereupon, and both the optical imaging system and the microtomography imaging system can be adapted to image the plurality of separate imaging objects simultaneously. In addition, one or more mirrors can be positioned at one or more sides of the imaging object or objects and arranged at an angle with respect to the rotating table such that one or more side views of the imaging object or objects are reflected upward toward the camera.

In still further embodiments, various methods of imaging a separate imaging object by multiple different imaging systems can include the process steps of placing the separate imaging object atop a rotating table adapted to support the imaging object at a single location during a multi-modal imaging process, obtaining one or more optical images of the imaging object while the imaging object is atop the rotating table, activating a secondary imaging system, obtaining one or more secondary images of the imaging object while the imaging object remains atop the rotating table and the secondary imaging system is activated, and rotating the rotating table about a vertical axis running therethrough to a plurality of different rotational positions during the imaging process. In particular, the one or more optical images can be obtained along a first direction with respect to the imaging object, while the secondary imaging system is located and captures images of the imaging object in a direction that is orthogonal with respect to the first direction. In some embodiments, the secondary imaging system comprises a microtomography imaging system. The method can also include transilluminating the imaging object from below while the imaging object remains atop the rotating table. In addition, the one or more optical images can be combined with the one or more secondary images using a processing device in logical communication with both the optical imaging system and the secondary imaging system.

Other apparatuses, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The included drawings are for illustrative purposes and serve only to provide examples of possible structures and arrangements for the disclosed inventive systems and methods for obtaining images of an imaging object using different imaging systems at a single location. These drawings in no way limit any changes in form and detail that may be made to the invention by one skilled in the art without departing from the spirit and scope of the invention.

DETAILED DESCRIPTION

Exemplary applications of apparatuses and methods according to the present invention are described in this section. These examples are being provided solely to add context and aid in the understanding of the invention. It will thus be apparent to one skilled in the art that the present invention may be practiced without some or all of these specific details. In other instances, well known process steps have not been described in detail in order to avoid unnecessarily obscuring the present invention. Other applications are possible, such that the following examples should not be taken as limiting.

In the following detailed description, references are made to the accompanying drawings, which form a part of the description and in which are shown, by way of illustration, specific embodiments of the present invention. Although these embodiments are described in sufficient detail to enable one skilled in the art to practice the invention, it is understood that these examples are not limiting; such that other embodiments may be used, and changes may be made without departing from the spirit and scope of the invention.

The invention relates in various embodiments to a multi-modal imaging system adapted to take and process different types of images of an imaging object while the object remains at the same location. Such an imaging object can be an animal, such as a mouse or other lab animal, and can be sedated or otherwise alive during the imaging processes. Of course, other imaging objects can also be similarly used in a system that is the same or substantially similar to that which is disclosed herein, and it is contemplated that any and all such suitable alternative imaging objects can also be used. In a particular detailed example, such as that which is provided herein for purposes of illustration, such a multi-modal imaging system can include an optical imaging system and a microtomography or other x-ray based imaging system, although other types of imaging systems may also be used.

Such a system using x-ray imaging can be preferable to structured light based systems, since the x-ray imaging works regardless of fur or color conditions, and also has the benefit of giving the complete surface of the imaging object. Such improvements lead to improved diffuse optical tomography reconstructions, and this arrangement can be accomplished using the various components and techniques disclosed herein.

Introduction

Figure 1A:
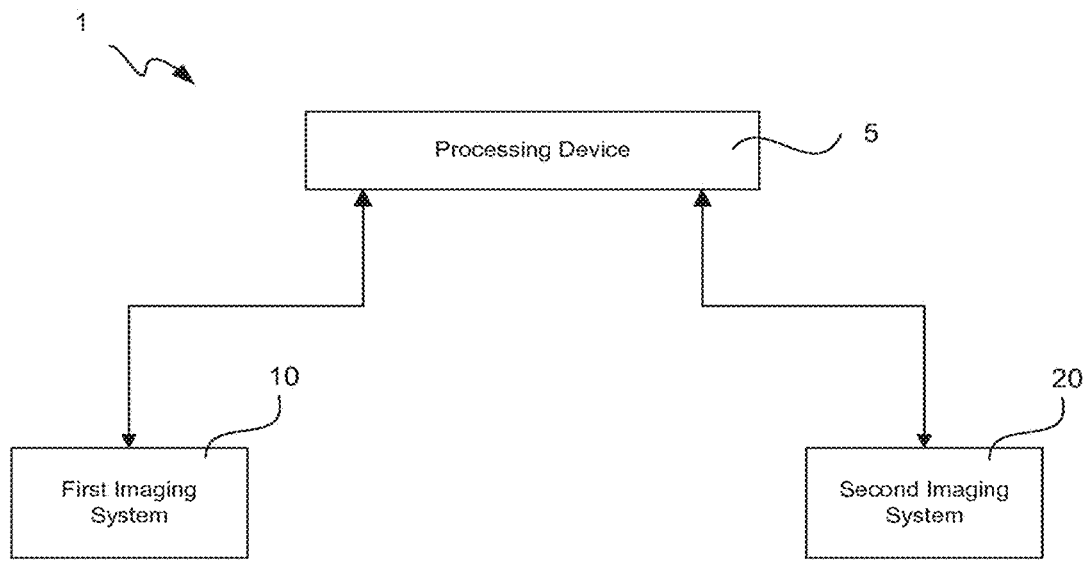
FIG. 1A illustrates in block diagram format an exemplary multi-modal imaging system adapted to provide multiple different modes of imaging for a given imaging object.

Referring first to FIG. 1A, an exemplary multi-modal imaging system adapted to provide multiple different modes of imaging for a separate imaging object is shown in block diagram format. Multi-modal imaging system 1 comprises a first imaging system 10, a second imaging system 20, and at least one processing device 5 adapted to control one or more of the imaging systems, and/or to process together multiple images obtained from the different imaging systems. While the present invention is primarily described herein with respect to combining data from two imaging systems, multi-modal imaging system 1 may include more than two imaging systems, and the illustrative embodiment is not meant to limit the number of imaging systems that are so combined. Details of a multi-modal imaging system are described in commonly owned U.S. Pat. No. 7,190,991 entitled "Multi-Mode Internal Imaging," which is incorporated herein in its entirety and for all purposes.

First imaging system 10 and second imaging system 20 can both employ any one of a variety of imaging modes, and each imaging system 10, 20 preferably uses a mode of imaging that is different that the other imaging system(s) in multi-modal imaging system 1. Exemplary imaging systems include, for example, various light imaging systems such as photographic, bioluminescent, and/or fluorescent imaging systems, as well as other types of imaging systems, such as MRI systems, CT systems, CAT scan systems, X-ray systems, ultrasound systems, nuclear medicine imaging systems such as positron emission tomography ("PET") systems, single photon emission computed tomography ("SPECT") systems, among other possible imaging systems.

First imaging system 10 and second imaging system 20 may produce spatial and/or functional information. Spatial information refers to information that contributes to a 2-D (pictorial) or 3-D geometric description of the object or its internal portions. A spatial representation provides a user with a 2-D or 3-D pictorial reference of the specimen. A 3-D geometric description typically comprises a reconstruction manufactured by processing data from multiple 2-D images. Functional information refers to information that contributes an item or activity of interest within the object. In one embodiment, one of the included imaging systems produces a 2-D or 3-D representation of a bioluminescent light source inside a mouse. The bioluminescent source may correspond to a wide variety of physiological issues being tracked or tested within the mouse, such as progress tracking of a particular cancer within a mouse, or activation of a specific gene. Some imaging applications include analysis of one or more representations of light emissions from internal portions of a specimen superimposed on a spatial representation of the specimen. The luminescence representation indicates portions of a specimen where an activity of interest may be taking place.

Figure 1B:
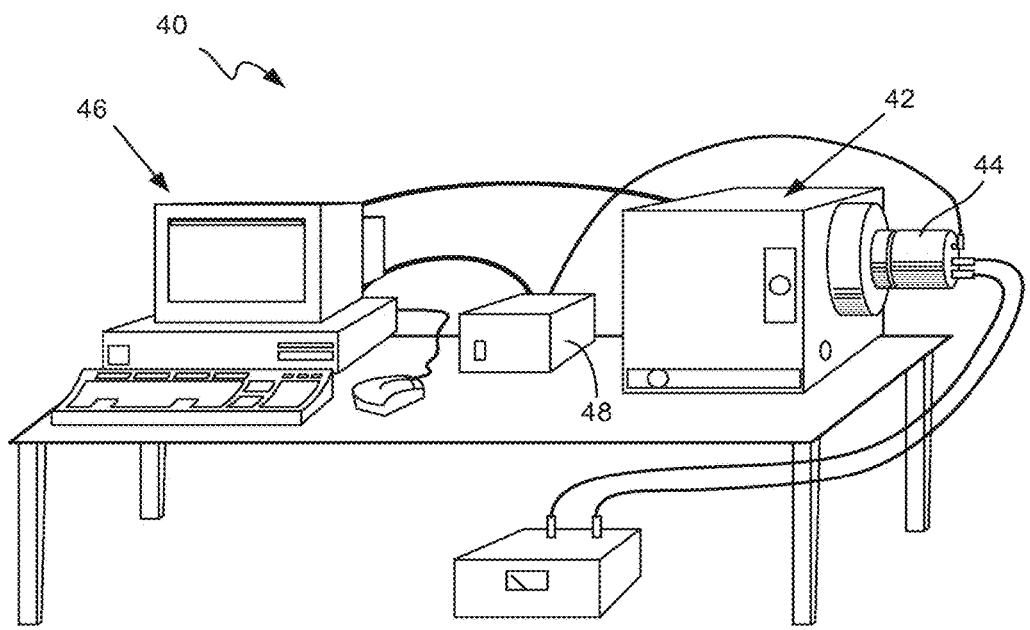
FIG. 1B illustrates in front perspective view an exemplary optical imaging system adapted to produce a 2-D or 3-D representation with respect to a given imaging object.

FIG. 1B illustrates in front perspective view an exemplary optical imaging system adapted to produce a 2-D or 3-D representation with respect to an imaging object. Optical imaging system 40, which can correspond to first imaging system 10 from FIG. 1A, may be used for a variety of imaging tasks, including the capture of photographic, luminescent and structured light images. Optical imaging system 40 can be, for example, a light imaging system that involves the capture of low intensity light—often on the order of about $10^3$ to about $10^{10}$ photons/second/centimeter squared/steradian—from a light-emitting object. The low intensity light may be emitted from any of a variety of light sources about or within the imaged object. For example, the light source may correspond to luciferase expressing cells within a living specimen, such as a mouse. The light source indicates portions of the sample, such as traced molecules in a particular portion of a living specimen, where an activity of interest may be taking place. As will be readily appreciated, such light imaging can involve bioluminescent imaging, fluorescent imaging, and/or any other suitable type of imaging.

As shown, light imaging system 40 can include an imaging chamber 42 adapted to receive a light-emitting sample in which low intensity light is to be detected. A high sensitivity camera 44, such as an intensified or a charge-coupled device ("CCD") camera, can be coupled with the imaging chamber 42. Camera 44 can be capable of capturing luminescent, photographic (i.e., reflection based images) and structured light images of an imaging object within imaging chamber 42. A computer 46 and its inclusive processor 5 working with light imaging system 40 may perform processing and imaging tasks such as obtaining, analyzing and manipulating 2-D or 3-D light source representations. An image processing unit 48 optionally interfaces between camera 44 and computer 46, and can be used to help generate composite images, such as combination photographic and luminescent images.

Light imaging systems 40 suitable for use with the present invention are available from Caliper Life Sciences of Hopkinton, Mass. Several light imaging systems suitable for use with the present invention are described in commonly owned U.S. Pat. No. 7,113,217 entitled "Multi-View Imaging Apparatus," which is incorporated by reference herein for all purposes. 3-D imaging systems suitable for use with the present invention are further described in commonly owned U.S. Pat. No. 7,616,985 entitled "Method and Apparatus for 3-D Imaging of Internal Light Source," which is also incorporated by reference herein for all purposes. Various approaches to generating composite photographic/luminescence images, such as might be desired from the foregoing systems are described in U.S. Pat. No. 5,650,135 issued to Contag et al. on Jul. 22, 1997, which is incorporated herein in its entirety and for all purposes.

Figure 2A:
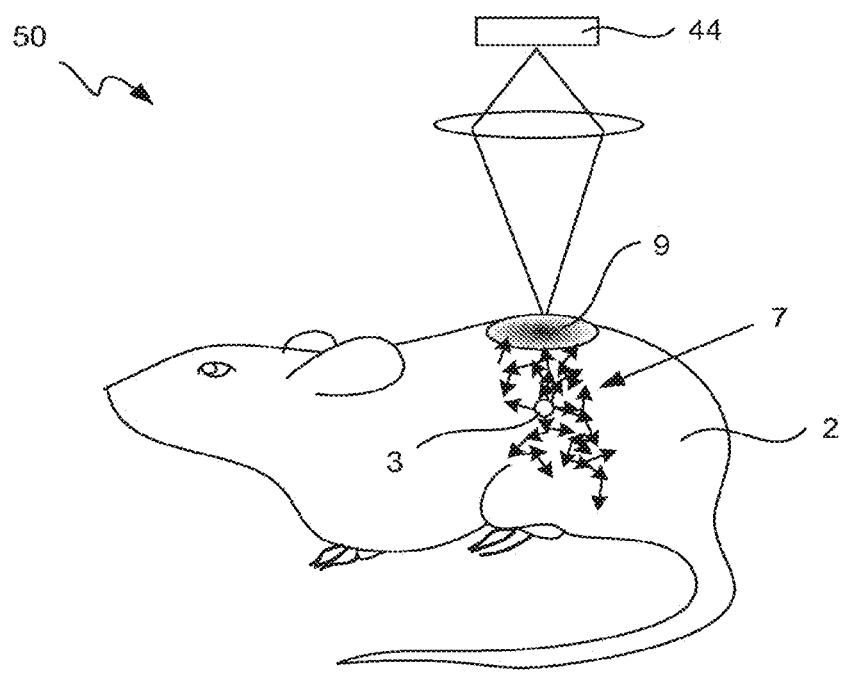
FIG. 2A illustrates a simplified pictorial of diffusive light propagation through and out from an imaging object.

Moving next to FIG. 2A, a simplified pictorial 50 of diffusive light propagation through and out from an imaging object is provided. Imaging object 2 can be, for example, a mouse or other mammal Mouse 2 can include one or more internal probes 3, which produce light that propagates through and out of the mouse. Internal probe 3 generally refers to any object or molecule that produces light, such as fluorescent or bioluminescent light. In the case of fluorescence, internal probe 3 absorbs incident energy of a certain wavelength or wavelength range and, in response, emits light energy at a different wavelength or wavelength range. In some embodiments, internal probe 3 can emits low-intensity fluorescent light. For example, a low intensity fluorescent probe of the present invention can emit light within mouse 2 in the range of about $10^4$ to about $10^{14}$ photons/second, depending on probe concentration and excitation light intensity. For some imaging systems, a fluorescent probe 3 that emits flux in the range of about $10^4$ to about $10^{10}$ photons/second is suitable, while other light fluxes are also permissible.

Animal tissue is a turbid medium, such that photons are both absorbed and scattered as they propagate through tissue. Photons 7 from internal probe or source 3 scatter and travel through tissue in the mouse 2 to one or more surfaces 9. The light emitted from the surface 9 may then be detected by a camera, such as CCD camera 44 from an optical imaging system.

Figure 2B:
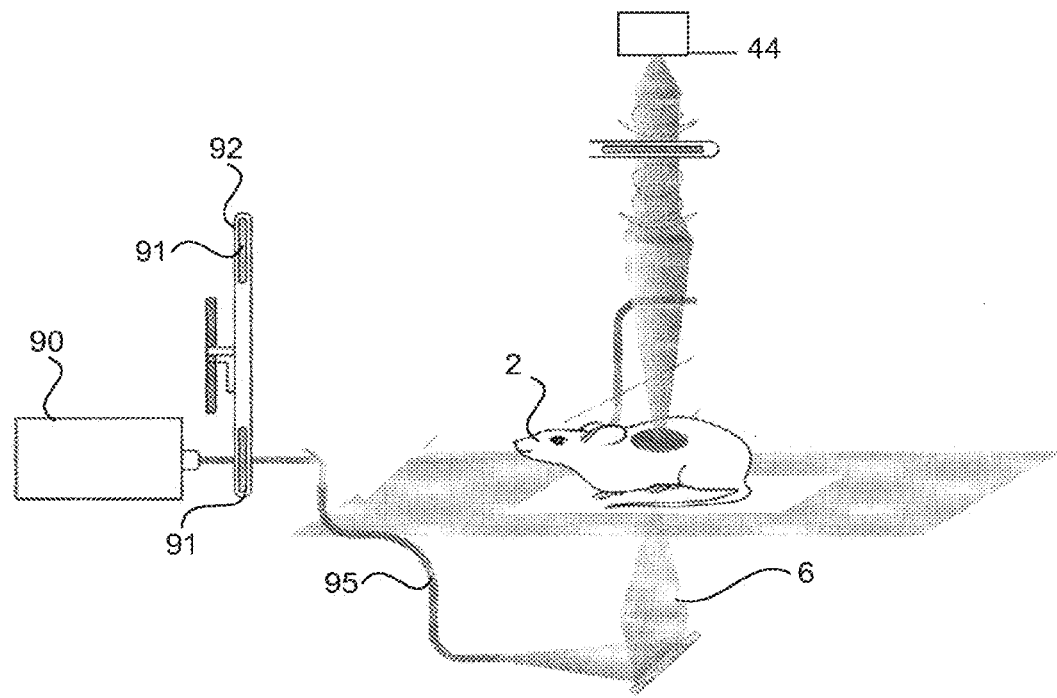
FIG. 2B illustrates an exemplary schematic of transillumination of an imaging object.

Continuing with FIG. 2B an exemplary schematic of transillumination of an imaging object is provided. In general, transillumination provides light from a side of an imaging object 2 that is opposite the camera 44 (e.g., incident light from below and a camera above), or into a portion of the object not visible to the camera, such that excitation and emission light cumulatively travels through the mouse or other imaging object. This can result in lower levels of autofluorescence and improved efficiency of excitation. Also, the ability to move the transillumination point, relative to a fluorescent probe fixed within the animal, provides additional information that can be used for 3D tomographic reconstructions.

As shown, the excitation light source can include a lamp 90 that provides light that passes through a filter 91 in excitation filter wheel 92, which allows a user to change the wavelength band of incident excitation light by changing which filter intercepts the incoming excitation light. The excitation light can be directed along fiber bundle or cable 95 towards a bottom surface of the mouse 2, where transillumination light 6 is then projected onto the mouse. In one embodiment, the outlet position of path 95 can be moved or re-directed to create multiple incident excitation light locations of transillumination path 95. Light can then propagate through the mouse 2 and be detected by camera 44. Although particular arrangements for diffusive light propagation and transillumination have been shown for purposes of illustration, it will be readily appreciated that other suitable arrangements can also be used. Further, it will be readily appreciated that other optical imaging types and systems can also be used with the multi-modal imaging systems disclosed herein. For example, epi-illumination of the imaging object 2 can be used, which can involve the use of an epi-illumination system or arrangement. One particular example of such an ep-illumination system arrangement can be found at commonly owned U.S. patent application Ser. No. 11/844,920, entitled, "Spectral Unmixing for In-Vivo Imaging," which is incorporated herein in its entirety and for all purposes. Bioluminescent imaging can also be undertaken.

Integrated Imaging Systems

In addition to the foregoing exemplary types of optical imaging systems, it is specifically contemplated that additional types of imaging also be provided in the same integrated system. In particular, integrated multi-modal imaging systems are provided that permit multiple types of images of an imaging object without any need to transfer the object between separate imaging systems. That is, in addition to an optical or other first type of imaging, a second type of imaging is also provided at the same location as the first type of imaging. Such a second type of imaging can be provided by, for example, a microtomography or other x-ray imaging system.

Figure 3:
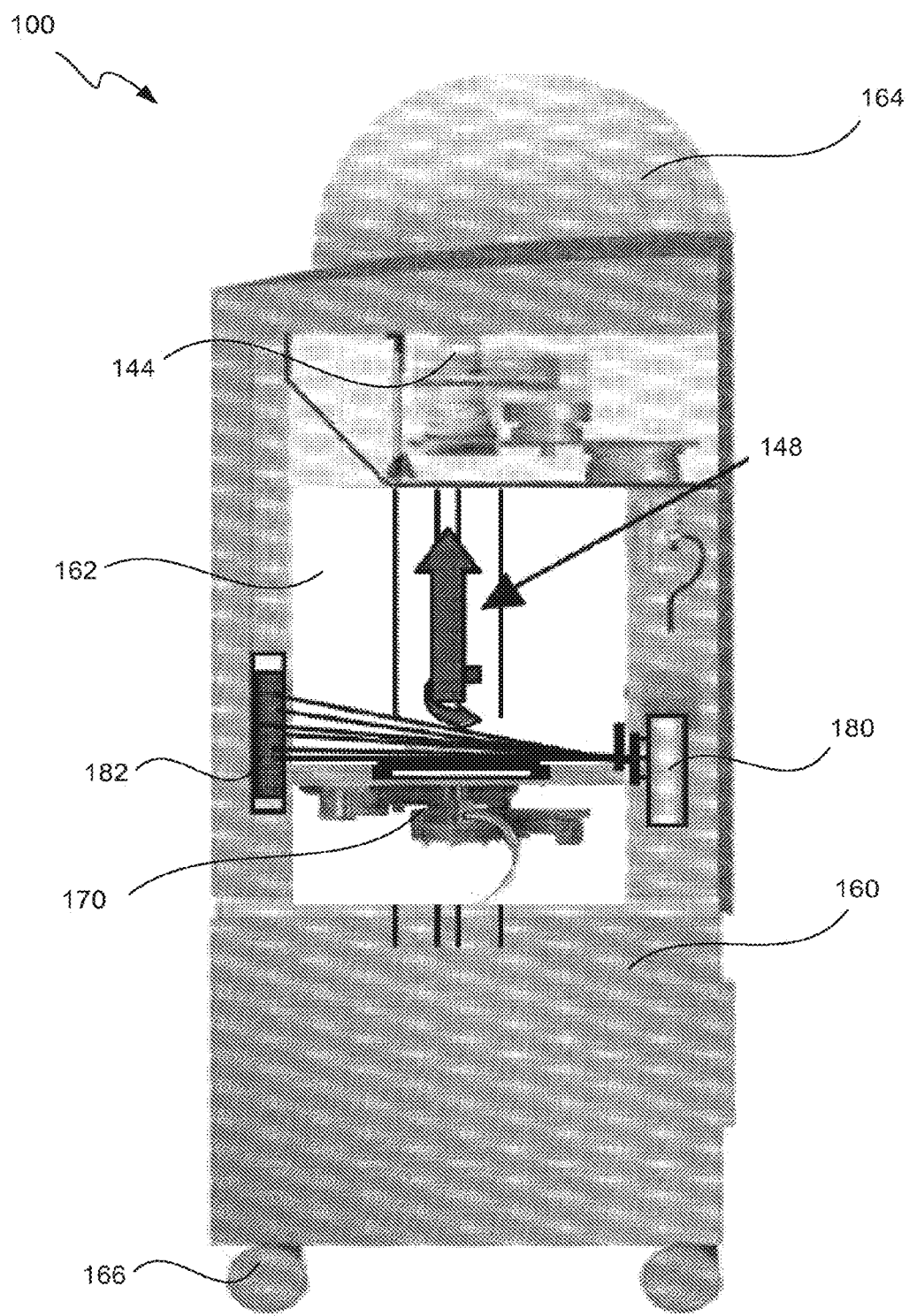
FIG. 3 illustrates in side cross-sectional view an exemplary integrated microtomography and optical imaging system according to one embodiment of the present invention.

Turning now to FIG. 3, an exemplary integrated microtomography and optical imaging system according to one embodiment of the present invention is illustrated in side cross-sectional view. Integrated system 100 can include imaging components to facilitate both optical imaging and microtomography imaging. Optical imaging components can include, for example, trans-illumination hardware 170 located beneath a table supporting an imaging object, and a camera 144 located above the imaging object along a vertical axis or distance 148, among other possible components. Microtomography components can include, for example, an x-ray source 180 and one or more x-ray receptors or sensors, such as x-ray flat panel 182, among other possible components.

The imaging object, stage, table and other various components can all be included within an imaging chamber 162, while the chamber, its contents and all of the other integrated system items and components can be contained within an outer cabinet 160. Outer cabinet 160 can also include an upper portion 164 adapted to house various optical system components, such as the camera, its power source and/or its controller. Outer cabinet 160 can also include one or more wheels or coasters 166 such that the cabinet, and thus the entire system, can be readily portable.

Figure 4A:
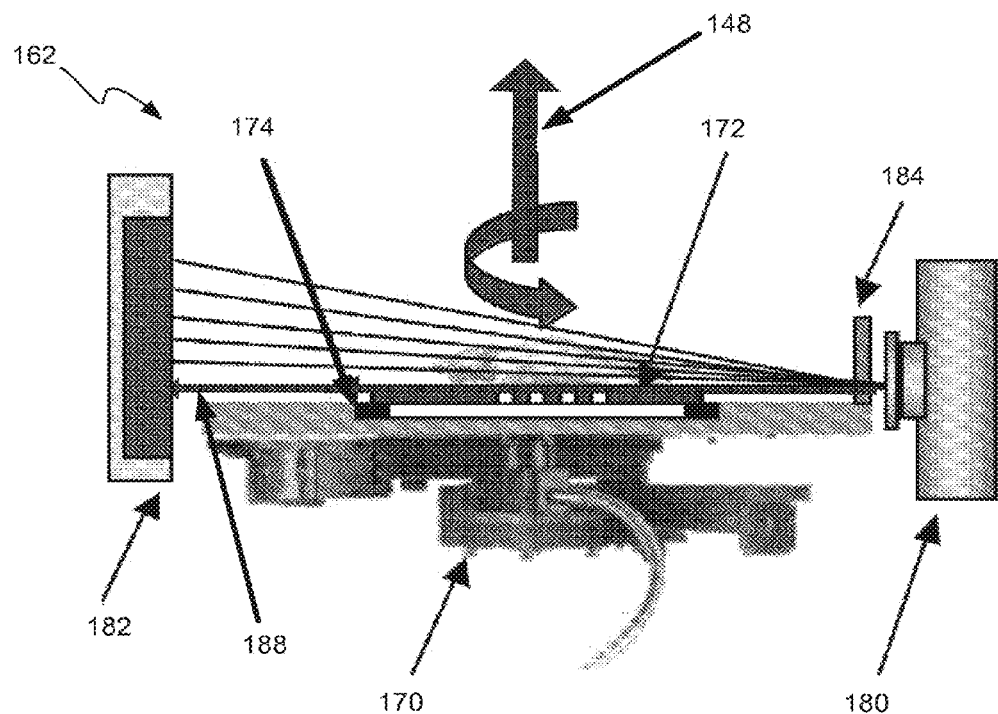
FIG. 4A illustrates in side cross-sectional view the stage portion of the imaging system of FIG. 3 according to one embodiment of the present invention.
Figure 4B:
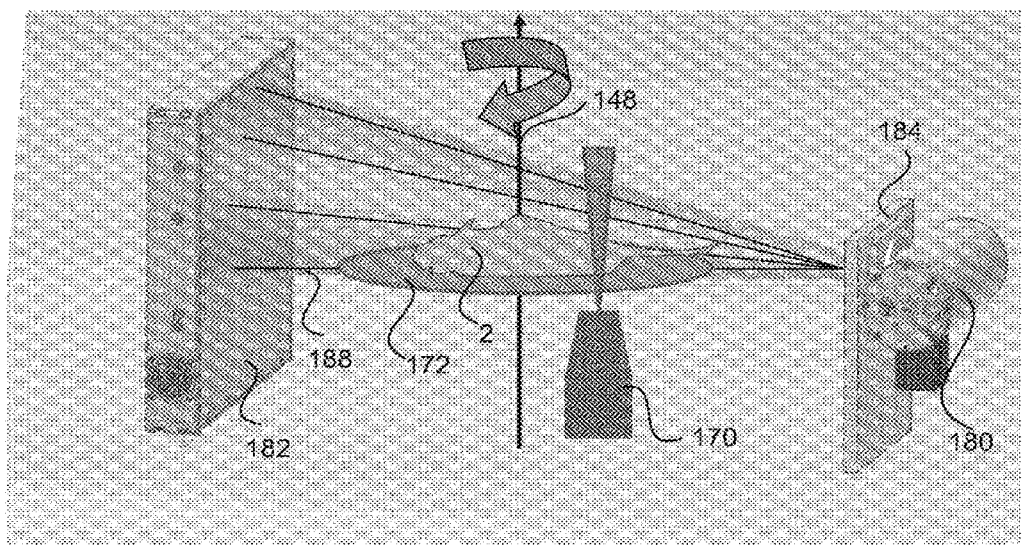
FIG. 4B illustrates in side perspective view the stage portion of the imaging system of FIG. 3 according to one embodiment of the present invention.

Moving now to FIGS. 4A and 4B, a close up of the stage portion of the imaging system of FIG. 3 is shown in side cross-sectional and side perspective views respectively. Depicted in FIGS. 4A and 4B are essentially the contents of imaging chamber 162, as well as various imaging components. An imaging object 2 can be placed atop a rotating table 172 that can be part of an overall stage adapted to support the imaging object. The stage can be situated above transillumination hardware 170, if that form of illumination is used, which hardware may be considered as part of the overall stage. In the event that transillumination is not desired, then different hardware or equipment that supports epi-illumination can alternatively be used. Table 172 can be adapted to rotate about a vertical axis 148 running therethrough, and an associated camera (not shown) can be situated above the rotating table along this vertical axis. One or more bearings 174 can be used to permit ease of rotation for the table 172 with respect to the rest of the overall stage.

As noted above, a secondary imaging system can include an x-ray type imaging system having an x-ray source 180 and an x-ray flat panel 182 or other x-ray detection component or array. A shutter 184 can be used to facilitate and control the incidence of x-rays from the source 180 to and through the imaging object 2 as it remains atop the table 172. As shown, the actual location of the x-ray source 180 can be spaced apart from and substantially horizontal with respect to the imaging object 2, such that a general incident direction 188 of the emitted x-ray beam is substantially horizontal or otherwise orthogonal with respect to the vertical axis 148.

Figure 5:
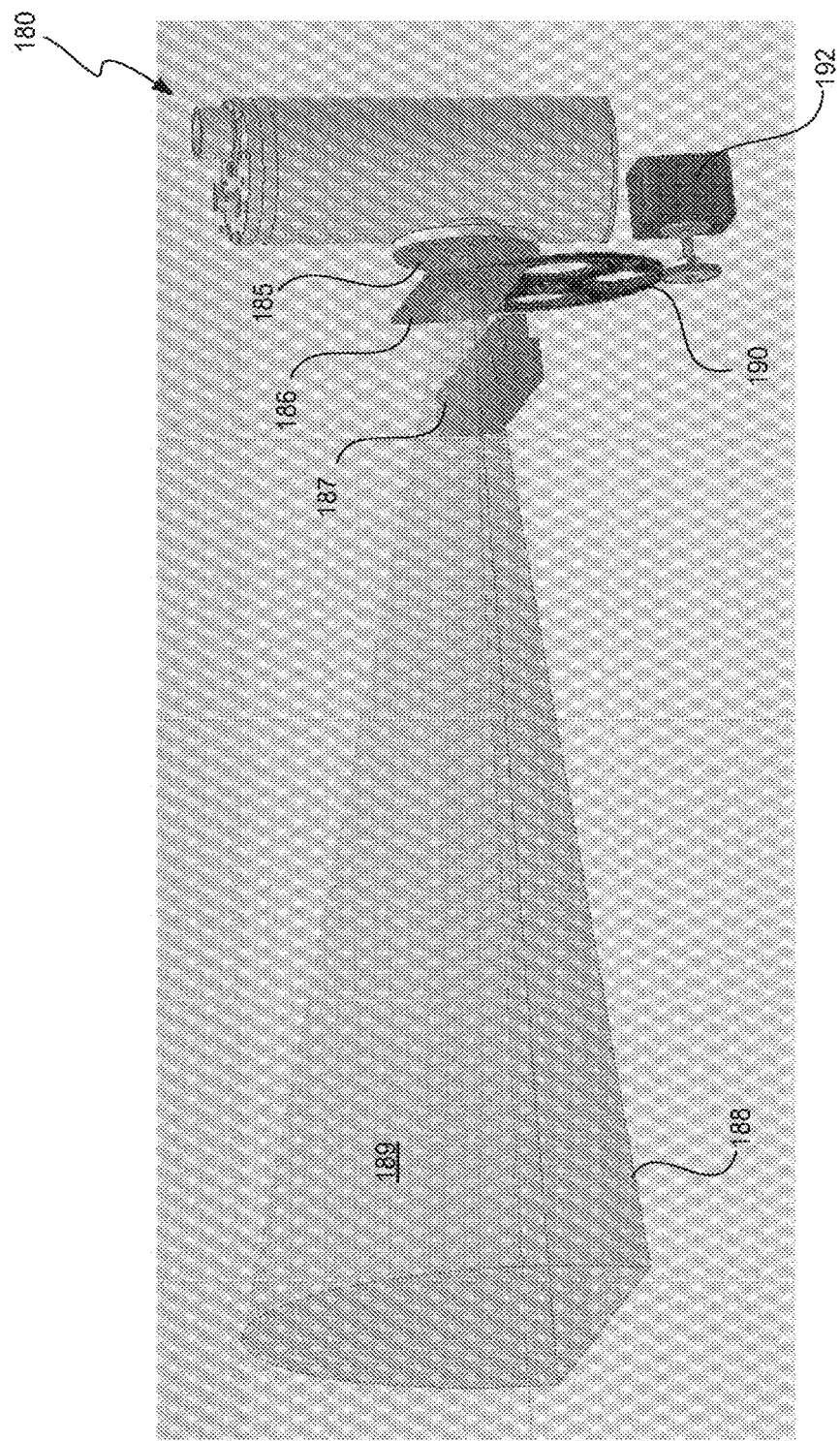
FIG. 5 illustrates in side perspective view an exemplary x-ray source and plurality of beam shapers according to one embodiment of the present invention.

As will be readily appreciated, a typical x-ray source 180 can tend to emit x-rays in a broad range of directions. Such an indiscriminate emission of x-rays, however, may cause some problems in a compact multi-modal imaging system, particularly where excess x-rays may damage and/or interfere with optical imaging equipment or illumination equipment, which can also lead to reflection and unwanted x-ray noise at the x-ray sensors. Turning next to FIG. 5, an exemplary x-ray source and plurality of x-ray beam shapers are illustrated in side perspective view. X-ray source 180 can be designed to emit x-rays from a side opening therefrom, whereupon the x-rays would ordinarily propagate in all directions. Instead of allowing this, one or more beam shaping devices can be used to limit the direction of the emitted x-ray beam, such that the x-rays pass through the object of interest, but are substantially above the hardware supporting the object.

Alternatively, or in addition to the simple shutter noted above, a plurality of beam shaping devices 185, 186, 187 can be used to block and shape the emitted x-ray beam. Such beam shaping devices 185, 186, 187 can be formed from any suitable x-ray blocking material, such as copper, for example. These devices can be sized, shaped and placed in such as way that the resulting x-ray beam 189 is shaped and directed in a manner that delivers a full amount of x-rays to and through the imaging object, but limits the amount of stray x-rays that could cause problems elsewhere within the multi-modal imaging system. As shown, beam shaper 185 generally limits the emitted x-rays into a cone shape in the direction of the imaging object. Beam shaper 186 can then be designed to further limit the cone, while beam shaper 187 can be designed to cut off the unneeded bottom portion of the cone that would extend below the rotating table and into any stage equipment, trans-illumination hardware and the like. Such a bottom cutoff can be at general incident horizontal direction 188, as shown. It will be readily appreciated that more or fewer beam shaping devices can be used, as may be desired for a particular design.

In addition to one or more beam shaping devices 185, 186, 187, a filter wheel 190 can be used to further limit or modify the emitted x-ray beam 189. One or more filters can be suitably installed within filter wheel 190, and the filter wheel can be driven by a motor 192 or other automated wheel adjusting device, as will be readily appreciated.

It is worth noting that that the substantially horizontal direction and location of the of the x-ray source, x-ray sensors, and x-ray beams with respect to the imaging object allows for the microtomography imaging to proceed unimpaired by the stage, rotating table, and any transillumination hardware that might be located underneath the imaging object, as well as the camera and other optical equipment located above the imaging object. In this type of arrangement using optical and x-ray imaging systems that are arranged along perpendicular or otherwise orthogonal axes, two disparate types of imaging systems can be combined to image simultaneously and effectively imaging objects at a single location. Of course, a given imaging object can be rotated to a plurality of different positions at the same single location, such as where a rotating table is used.

Although the figures show an optical imaging system arranged about a vertical axis and an x-ray imaging system arranged about a horizontal axis or field of view, it will be readily appreciated that the various hardware components can be rearranged to support reverse or alternate versions of such orthogonal axis that will also work well.

Due to the combined nature of integrated microtomography and optical imaging system 100, multiple different modes of imaging can be obtained with respect to an imaging object without needing to move the imaging object from system to disparate system. This advantageously avoids many of the problems that can be associated with imaging object transfer between systems. This also results in a more reliable and streamlined coordination of multiple imaging processing, as it can thus be known that images taken by both systems are on the same object as it is in the same object pose and position and/or rotational position of the supporting table.

In addition, the ability of the two different modes of imaging to operate together within a confined space results in a relatively compact system that can be assembled into a single portable outer housing or cabinet. This can be accomplished at least in part due to the orthogonal nature of the axes or directions of image taking with respect to the two or more different imaging systems. That is, where a combined system might provide for multi-modal imaging of an object along the same or parallel axes or directions, such an arrangement tends to be cumbersome and require a substantial amount of space. Conversely, the juxtaposition of disparate imaging equipment along orthogonal axes results in a more compact and efficient arrangement, which permits the ready portability of the integrated imaging system. Furthermore, the arrangement of the two disparate imaging systems along perpendicular or orthogonal axes results in little to no interference between the various hardware components of the microtomography or x-ray imaging system and the camera, illumination components and other hardware of the optical imaging system. This particular arrangement also results in no need for a large and expensive rotational gantry, such as that which is found in many traditional CT systems.

Figure 6A:
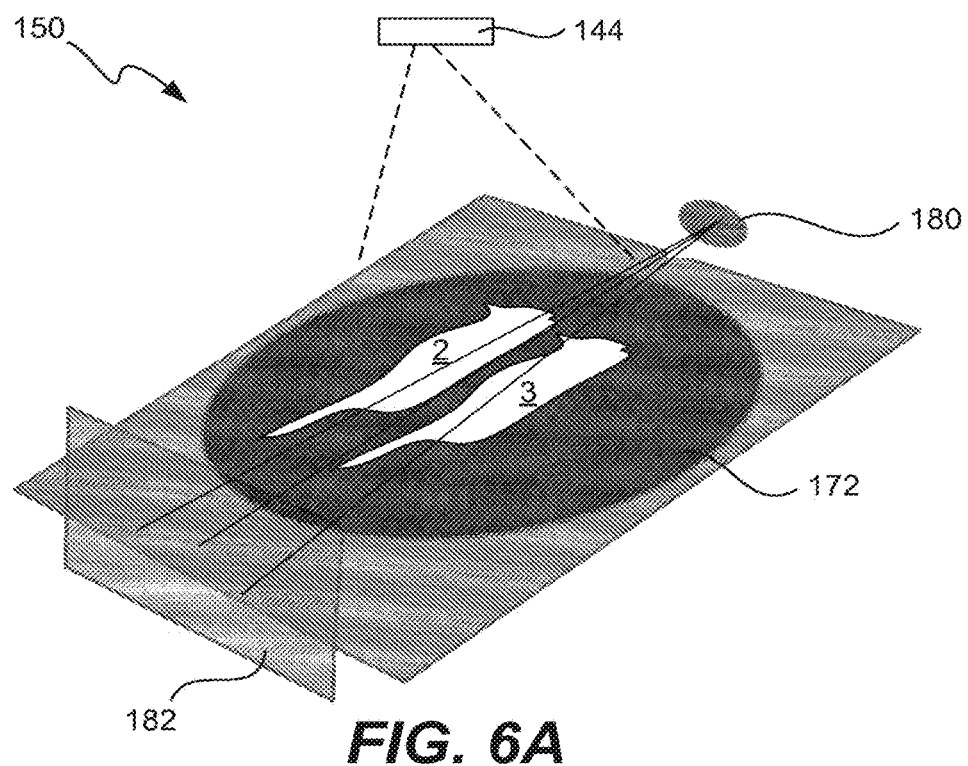
FIGS. 6A-6B illustrate in top perspective views an exemplary integrated microtomography and optical imaging system adapted to image multiple imaging objects simultaneously according to one embodiment of the present invention.
Figure 6B:
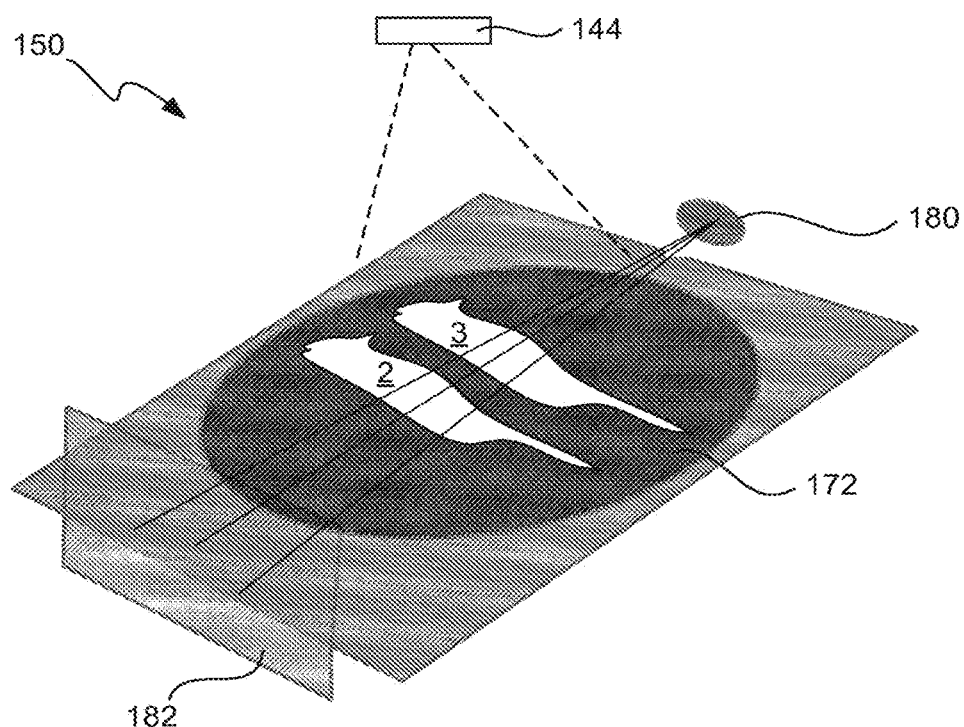
Figure 7:
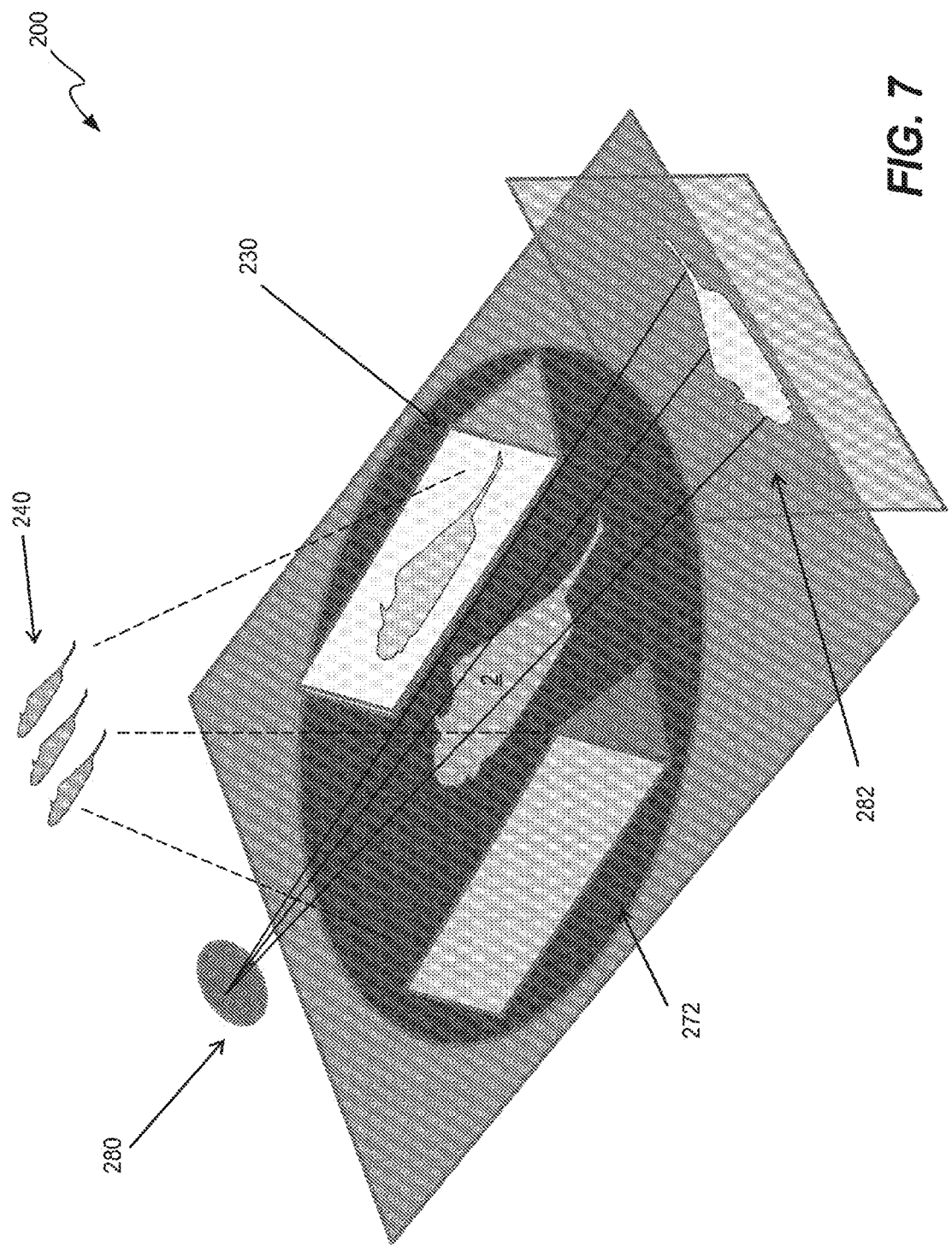
FIG. 7 illustrates in top perspective view an exemplary integrated microtomography and optical imaging system having side mirrors adjacent to the imaging object according to one embodiment of the present invention.

Additional features and benefits that can be realized through the use of the foregoing system are reflected in the alternative embodiments and features presented in FIGS. 6A, 6B and 7. Turning first to FIGS. 6A-6B an exemplary integrated microtomography and optical imaging system adapted to image multiple imaging objects simultaneously is illustrated in different top perspective views. As shown, integrated imaging system 150 can be identical or substantially similar to system 100 disclosed above. In particular, integrated imaging system 150 can similarly include imaging components to facilitate both optical imaging and microtomography imaging, such as, for example, a camera 144 and other optical imaging system components, an x-ray source 180, an x-ray flat panel or detector 182, and a rotating table 172, among other possible items.

Due to this particular choice of imaging technologies and their respective arrangements, the system can be adapted to image a plurality of imaging objects at the same time, as show with respect to imaging objects 2 and 3. Although imaging objects 2 and 3 are illustrated as two mice that are arranged side by side atop rotating table 172, it will be readily appreciated that the same technologies and arrangement can be used to image other types of imaging objects as well. As shown, the optical imaging system can readily capture one or more overhead images of the plurality of imaging objects 2, 3, while the microtomography imaging system can readily capture a series of x-ray images of the imaging objects at different rotational positions of the rotating table 172. Provided a sufficient number of x-ray images at different rotational positions are taken, the associated processing device or system can then be adapted to correlate and juxtapose the respective optical and x-ray imaging data such that three-dimensional reconstructions of both imaging objects 2, 3 can be provided. In this manner, multiple imaging objects can be imaged using multiple disparate types of imaging systems simultaneously, such that useful and accurate three-dimensional reconstructions of all imaging objects can be provided in an efficient process.

FIG. 7 illustrates in top perspective view an exemplary integrated microtomography and optical imaging system having side mirrors adjacent to the imaging object according to one embodiment of the present invention. As will be readily appreciated, many imaging objects can have length to width ratios that are not 1:1. This can result in loss of space inefficiencies where a rotating table is used. In addition, the use of an overhead camera as the only optical system camera can result in images that are limited in nature. These issues can be overcome by placing one or more side mirrors adjacent to the imaging object, which is accomplished in the improved system shown in FIG. 7.

Similar to the foregoing embodiments, integrated imaging system 200 can include imaging components to facilitate both optical imaging and microtomography imaging, such as, for example, an optical stage (not shown), a camera and other optical imaging system components 240, an x-ray source 280, an x-ray flat panel or detector 282, and a rotating table 272, among other possible items. A mouse or other suitable imaging object 2 can be placed at or near the center of the rotating table 272, and one or more side viewing mirrors 230 can be located proximate the imaging object. Such mirrors 230 can be located on the rotating table itself, as shown, or may be positioned off of the rotating table, if desired. Preferably, mirrors 230 can be designed such that side views of the imaging object are reflected upward to the overhead camera and other optical system components 240. In this case, three images of imaging object 2 are projected upward, representing overhead and two side views.

As shown, two triangular shaped and self-supporting mirrors 230 may be positioned atop the rotating table. Alternatively, other shapes, sizes and mirror arrangements can be used as well. Such a side mirror or mirrors 230 can be arranged at about a 45 degree angle with respect to the horizontally oriented rotating table 272, such that the side views of the imaging object 2 are projected upward in a direct vertical direction. Of course, adjustments in the angle of the mirrors can be made where such adjustments are preferable due to the exact positioning of the overhead camera. In the event that the camera is not directly overhead or is positioned at some other location, the angles of the side mirrors 230 can be adjusted accordingly.

In addition, mirrors 230 are preferably formed entirely from materials that are transparent to or otherwise non-interfering with x-rays. Such materials can be, for example, low density glass or plastic, along with a non-metallic ink or other dark backing on the back surface to facilitate reflection. In this manner, the mirrors 230 do not significantly interfere with the x-ray source 280 and detector 282 as the rotating table 272 rotates to its plurality of different positions.

Image Processing

As noted above with respect to FIG. 1, one or more processing devices 5 or systems can be used to process together multiple images and/or data obtained from different imaging systems. Such processing can include performing optical diffuse tomography reconstruction for an imaging object or objects, with such reconstruction involving the combination of optical and x-ray data. Various examples of and techniques for using a processing device or system to perform the relatively complex types of reconstruction required for such systems can be found at, for example, commonly owned U.S. Pat. No. 7,190,991 entitled "Multi-Mode Internal Imaging," U.S. Pat. No. 7,599,731 entitled "Fluorescent Light Tomography," U.S. Pat. No. 7,616,985 entitled "Method and Apparatus for 3-D Imaging of Internal Light Sources," and U.S. patent application Ser. No. 11/844,551, entitled, "Apparatus and Methods for Determining Optical Tissue Properties," each of which is incorporated herein in its entirety and for all purposes.

It is specifically contemplated that use of processing to combine images and/or data from a combined multi-modal optical and x-ray imaging system can involve a processing device or system that is in logical communication with both the optical imaging system and the microtomography or other x-ray imaging system. Such a processing device or system can be adapted to combine imaging data obtained by the optical imaging system with imaging data obtained by the microtomography imaging system by using techniques that involve:

processing x-ray imaging data obtained from the microtomography or other x-ray imaging system to yield a volumetric three-dimensional rendering of the imaging object, segmenting the x-ray imaging data to determine an x-ray surface mesh of the imaging object, mapping optical image data obtained from the optical imaging system onto the x-ray surface mesh of the imaging object, and processing the surface-mapped optical image data through a diffuse tomography algorithm to determine a three-dimensional distribution of light-emitting sources within the imaging object.

In addition to the above listed techniques, the processing device or system can be further adapted to provide additional functionalities that are specialized with respect to the combination of optical imaging data and microtomography imaging data. In particular, such additional specialized functionalities that can be provided by way of such a processing device or system can include:

determining an anatomical map of tissues within the imaging object using the volumetric microtomography data, and creating a heterogeneous tissue property map for use within the optical diffuse tomography algorithm using the anatomical map.

It is worth noting that the function of determining an anatomical map of tissues within the imaging object can be of great use where microtomography imaging is used rather than structured light or other forms of imaging in order to create a surface mesh of the imaging object.

Method of Use

Figure 8:
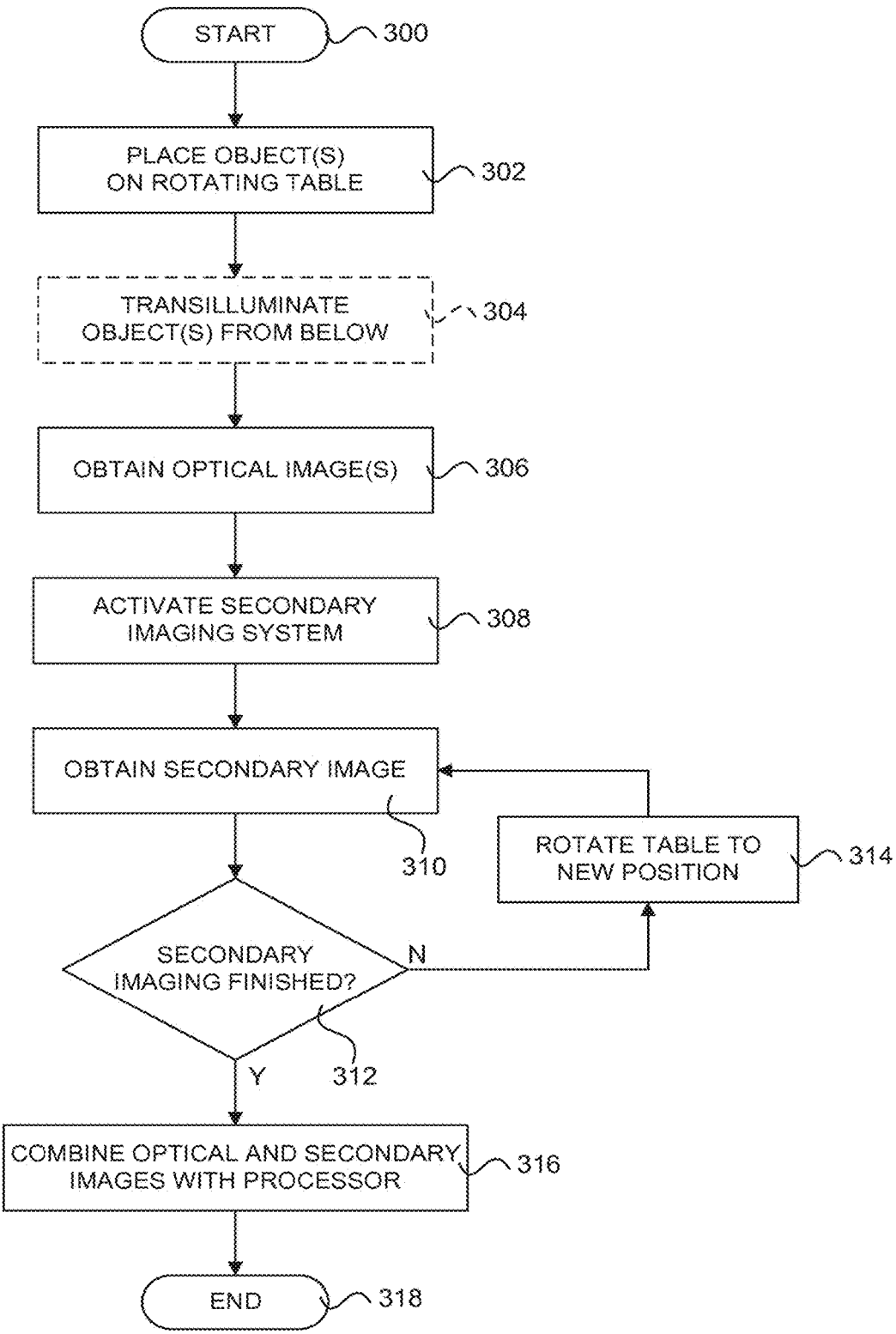
FIG. 8 presents a flowchart of an exemplary method of imaging an imaging object by multiple different imaging systems according to one embodiment of the present invention.

Turning lastly to FIG. 8, a flowchart of an exemplary method of imaging an imaging object by using multiple different imaging systems is provided. While the provided flowchart may be comprehensive in some respects, it will be readily understood that not every step provided is necessary, that other steps can be included, and that the order of steps might be rearranged as desired by a given device manufacturer, vendor or user. For example, step 306 may alternatively be performed after or simultaneously with steps 310-314. As another example, step 308 could be performed before or simultaneously with steps 304 and 306. Also, step 304 can be optional, and may be replaced with one or more other forms or directions of object illumination. Other suitable potential orders of steps will be readily appreciated.

After start step 300, process step 302 can involve placing the imaging object on a rotating table. Again, the rotating table can be adapted to support the imaging object at a single location during an integrated multi-modal imaging process, and the imaging object can be a mouse or other mammal. The imaging object can then optionally be transilluminated from below while it is on the rotating table at process step 304. Although the term "below" has been used, it will be readily appreciated that the transillumination should take place at a location by the imaging object that is opposite the location of an associated camera. As such, if the camera might be located below the imaging object, then the transillumination should be made from above the object. In the event that transillumination is not used, it will be readily appreciated that epi-illumination and/or bioluminescence of the imaging object can be alternatively performed for process step 304.

One or more optical images of the object can then be obtained at process step 306. Obtaining the optical images can take place while the object is being transilluminated, epi-illuminated and/or is emitting bioluminescence. Also, the optical images can be obtained along a first direction with respect to the imaging object. In some embodiments, this can be a vertical direction, such as where a camera is positioned above the imaging object. Where the rotating table rotates about a vertical axis running therethrough, it will be readily appreciated that the images are obtained substantially about such a vertical axis. Of course, it may not be necessary to rotate the horizontally oriented table in order to obtain one or more optical images from the camera located vertically above the imaging object, as will be readily appreciated.

At process step 308, a secondary imaging system can be activated. As noted above, such a secondary imaging system can be a microtomography or other suitable x-ray imaging system. In such cases, activating the secondary imaging system can involve turning on an x-ray source. This x-ray source (or other imaging source should a different secondary imaging system be used) can be located in a direction that is orthogonal with respect to the first direction. In some embodiments, this direction can be substantially horizontal with respect to the imaging object.

An x-ray or other secondary image of the object can then be obtained at process step 310. In the event of x-ray imaging, this can involve the use of an array of x-ray sensors positioned proximate the imaging object and opposite the x-ray source. As in the case of the optical imaging, the image is obtained while the imaging object remains atop the rotating table. At subsequent decision step 312, an inquiry is then made as to whether the secondary imaging is finished. If not, then the method continues to step 314, where the table is rotated to a new position. From step 314, the method reverts to step 310, where another secondary image is obtained. This cycle repeats until the inquiry result is yes at step 312.

When the inquiry result is yes, then the method continues to process step 316, where the optical and secondary imaging results are combined using a processing device. The method then ends at end step 318.

Although the foregoing invention has been described in detail by way of illustration and example for purposes of clarity and understanding, it will be recognized that the above described invention may be embodied in numerous other specific variations and embodiments without departing from the spirit or essential characteristics of the invention. Certain changes and modifications may be practiced, and it is understood that the invention is not to be limited by the foregoing details, but rather is to be defined by the scope of the appended claims.

What is claimed is:

1. An integrated microtomography and optical imaging system, comprising:

a rotating table configured to support an imaging object, and to rotate the imaging object about a first axis running through the imaging object to a plurality of different rotational positions;

an optical imaging apparatus configured to illuminate and obtain optical image information for the imaging object along one or more optical paths that are substantially parallel to the first axis while the imaging object is on the rotating table;

a microtomography imaging apparatus configured to obtain microtomographic image information for the imaging object along one or more radiation paths that are substantially orthogonal to the first axis while the imaging object is on the rotating table; and an electronic processor connected to the optical imaging apparatus and the microtomography imaging apparatus and configured to combine the optical image information and the tomographic image information to obtain a representation of a three-dimensional distribution of light-emitting sources within the imaging object, wherein the optical image information corresponds to at least one of fluorescence emission from the imaging object and bioluminescence emission from the imaging object.

2. The system of claim 1, wherein the optical imaging apparatus is configured to obtain optical image information comprising multiple simultaneous images of the imaging object, and wherein each of the simultaneous images corresponds to emission of light along a different direction from the imaging object.

3. The system of claim 2, wherein the multiple simultaneous images comprise three images, and wherein each of the three images corresponds to direction of light emission angularly displaced by at least 90 degrees from directions of light emission corresponding to the others of the three images.

4. The system of claim 2, wherein the optical imaging apparatus comprises one or more reflective elements positioned on the rotating table to direct light emitted from the imaging object along directions that are substantially parallel to the first axis.

5. The system of claim 1, wherein the optical imaging apparatus is configured to illuminate the imaging object and obtain image information from a common side of the imaging object.

6. The system of claim 1, wherein the optical imaging apparatus is configured to illuminate the image object and obtain image information from opposite sides of the imaging object.

7. The system of claim 1, wherein during operation of the system, the electronic processor is configured to:
direct the rotating table to position the imaging object at multiple angular orientations about the first axis;
for each of the angular orientations, activate the optical imaging apparatus to obtain optical image information for the imaging object;
for each of the angular orientations, activate the microtomographic imaging apparatus to obtain microtomographic image information for the imaging object; and
combine the optical image information and microtomographic image information for each of the angular orientations to obtain the representation of the three-dimensional distribution of light-emitting sources within the imaging object.

8. The system of claim 1, wherein the microtomography imaging apparatus comprises an x-ray source and an x-ray detector.

9. The system of claim 1, wherein the microtomography imaging apparatus is configured to detect positron emission from the imaging object to obtain the microtomographic image information.

10. The system of claim 1, wherein the microtomography imaging apparatus is configured to measure acoustic scattering from the imaging object to obtain the microtomographic image information.

11. The system of claim 1, wherein the electronic processor is configured to obtain the representation of the three-dimensional distribution of light-emitting sources within the imaging object by:
determining a three-dimensional representation of the imaging object from the microtomographic image information;
constructing a surface mesh of the imaging object from the three-dimensional representation;
map the optical image information onto the surface mesh of the imaging object; and
apply a diffuse tomographic reconstruction algorithm to the mapped optical image information to obtain the representation of the three-dimensional distribution of light-emitting sources within the imaging object.

12. The system of claim 1, wherein:
the rotating table is configured to support a plurality of imaging objects simultaneously;
the optical imaging apparatus is configured to illuminate and obtain optical image information for each one of the plurality of imaging objects;
the microtomography imaging apparatus is configured to obtain microtomographic image information for each one of the plurality of imaging objects; and
the electronic processor is configured to combine the optical image information and tomographic image information for each one of the plurality of imaging objects to obtain a representation of a three-dimensional distribution of light-emitting sources within each one of the imaging objects.

13. The system of claim 1, wherein the microtomography imaging apparatus comprises an x-ray radiation source and at least one x-ray beam shaping device.

14. The system of claim 1, wherein the imaging object is elongated along a first direction, and wherein the rotating table is configured to support the imaging object so that the first direction is parallel to a plane defined by the rotating table, and orthogonal to the first axis.

15. The system of claim 1, wherein the imaging object is an animal having an elongated body form, and wherein the first axis is substantially orthogonal to a direction of elongation of the animal.

16. A method, comprising:
rotating an imaging object about a firk axis to a plurality of different rotational positions;
at each of the rotational positions, illuminating the imaging object and obtaining optical image information for the imaging object along one or more optical paths that are substantially parallel to the first axis, wherein the optical image information corresponds to at least one of fluorescence emission from the imaging object and bioluminescence emission from the imaging object;
at each of the rotational positions, obtaining microtomographic image information for the imaging object along one or more radiation paths that are substantially orthogonal to the first axis; and
combining the optical image information and the tomographic image information to obtain a representation of a three-dimensional distribution of light-emitting sources within the imaging object.

17. The method of claim 16, further comprising, at each of the rotational positions, obtaining optical image information comprising multiple simultaneous images of the imaging object, wherein each of the simultaneous images corresponds to emission of light along a different direction from the imaging object.

18. The method of claim 16, further comprising illuminating the imaging object and obtaining the optical image information for the imaging object from a common side of the imaging object.

19. The method of claim 16, further comprising illuminating the imaging object and obtaining the optical image information for the imaging object from opposite sides of the object.

20. The method of claim 16, wherein the microtomographic image information comprises information derived from one or more x-ray images of the imaging object.

* * * * *

UNITED STATES PATENT AND TRADEMARK OFFICE
CERTIFICATE OF CORRECTION

PATENT NO.        : 9,770,220 B2
APPLICATION NO.   : 15/098819
DATED             : September 26, 2017
INVENTOR(S)       : Daniel G. Stearns et al.

Page 1 of 1

It is certified that error appears in the above-identified patent and that said Letters Patent is hereby corrected as shown below:

Column 16
Line 48, in Claim 16, delete "firk" and insert -- first --

Signed and Sealed this
Fourteenth Day of August, 2018

Andrei Iancu
*Director of the United States Patent and Trademark Office*